(12) United States Patent
Reed

(10) Patent No.: US 7,160,860 B2
(45) Date of Patent: Jan. 9, 2007

(54) USE OF INTERLEUKIN-6 ANTAGONISTS FOR THE TREATMENT OF DISEASES CHARACTERIZED BY HIGH LEVELS OF AROMATASE

(75) Inventor: Michael John Reed, London (GB)

(73) Assignee: Sigma Tau Industrie Farmaceutiche Riunite S.p.A., Rome (IT)

( * ) Notice: Subject to any disclaimer, the term of this patent is extended or adjusted under 35 U.S.C. 154(b) by 170 days.

(21) Appl. No.: 10/988,628

(22) Filed: Nov. 16, 2004

(65) Prior Publication Data

US 2005/0090443 A1  Apr. 28, 2005

Related U.S. Application Data

(62) Division of application No. 10/220,183, filed as application No. PCT/IT00/00072 on Mar. 6, 2000, now abandoned.

(51) Int. Cl.
*A61K 38/00* (2006.01)
(52) U.S. Cl. ........................................................ 514/12
(58) Field of Classification Search ................... 514/12
See application file for complete search history.

(56) References Cited

FOREIGN PATENT DOCUMENTS

| WO | WO 96/34104 | 10/1996 |
|---|---|---|
| WO | WO-96/34104 | * 10/1996 |
| WO | WO 96/44104 | 10/1996 |
| WO | WO 98/13383 | 4/1998 |
| WO | WO 98/15283 | 4/1998 |

OTHER PUBLICATIONS

On-Line Medical Dictionary (http://cancerweb.ncl.ac.uk/cgi-bin/omd?query=aromatase; Dec. 12, 1998).*
Henry et al., "Molecular Markers of Malignant Neoplasms", in Clinical Diagnosis and Management by Laboratory Methods, 1991, pp. 302-303.*
Ehlers et al. "Combining two mutations of human interleukin-6 that affect gp 130 activation results in a potent interleukin-6 receptor antagonist on human myeloma cells" J. Biol. Chem. 270:8158-8163 (1995).
Paonessa et al. "Two distinct and independent sites on IL-6 trigger gp130 dimer formation and signalling" EMBO J. 14:1942-1951 (1995).
Reed et al. "Breast cancer and the role of cytokines in regulating estrogen synthesis: An emerging hypothesis" Endocr. Rev. 18:701-715 (1997).

* cited by examiner

*Primary Examiner*—Bruce Campell
*Assistant Examiner*—Maury Audet
(74) *Attorney, Agent, or Firm*—Nixon & Vanderhye, P.C.

(57) ABSTRACT

The invention described herein relates to the use of human interleukin-6 antagonists, totally incapable of binding to gp 130, as specific inhibitors of the enzyme aromatase, useful for the treatment of hormone-dependent tumours, and particularly tumours of the breast.

8 Claims, 4 Drawing Sheets

Effect of Sant 7 on IL-6 + IL-6sR Stimulated Aromatase activity

Dose response for the effect of Sant 7
On IL-6 + IL-6sR stimulated aromatase

SEQUENCE LISTING

<160> NUMBER OF SEQ ID NOS: 12

<210> SEQ ID NO 1
<211> LENGTH: 184
<212> TYPE: PRT
<213> ORGANISM: Homo sapiens

<400> SEQUENCE: 1

```
Pro Val Pro Pro Gly Glu Asp Ser Lys Asp Val Ala Ala Pro His Arg
1               5                   10                  15

Gln Pro Leu Thr Ser Ser Glu Arg Ile Asp Lys Gln Ile Arg Asp Ile
            20                  25                  30

Leu Asp Phe Ile Ser Ala Leu Arg Lys Glu Thr Cys Asn Lys Ser Asn
        35                  40                  45

Met Cys Glu Ser Ser Lys Glu Ala Leu Ala Glu Asn Asn Leu Asn Leu
    50                  55                  60

Pro Lys Met Ala Glu Lys Asp Gly Cys Phe Gln Ser Gly Phe Asn Glu
65                  70                  75                  80

Glu Thr Cys Leu Val Lys Ile Ile Thr Gly Leu Leu Glu Phe Glu Val
                85                  90                  95

Tyr Leu Glu Tyr Leu Gln Asn Arg Phe Glu Ser Ser Glu Glu Gln Ala
            100                 105                 110

Arg Ala Val Gln Met Arg Thr Lys Asp Leu Ile Gln Phe Leu Gln Lys
        115                 120                 125

Lys Ala Lys Asn Leu Asp Ala Ile Thr Thr Pro Asp Pro Thr Thr Asn
    130                 135                 140
```

```
Ala Ser Leu Leu Thr Lys Leu Gln Ala Gln Asn Gln Trp Leu Gln Asp
145                 150                 155                 160

Ile Thr Thr His Leu Ile Leu Arg Ser Phe Lys Glu Phe Leu Gln Ser
                165                 170                 175

Ser Leu Arg Ala Leu Arg Gln Met
            180
```

<210> SEQ ID NO 2
<211> LENGTH: 60
<212> TYPE: DNA
<213> ORGANISM: Artificial Sequence
<220> FEATURE:
<223> OTHER INFORMATION: Mutagenetic primer IL-6 160R/157WR

<400> SEQUENCE: 2

```
cgctgacgaa gcttcaggca cagaaccagy ggctgcagcg tatgacaact gatctcattc    60
```

<210> SEQ ID NO 3
<211> LENGTH: 64
<212> TYPE: DNA
<213> ORGANISM: Artificial Sequence
<220> FEATURE:
<223> OTHER INFORMATION: Mutagenic primer IL-6 T162D

<400> SEQUENCE: 3

```
gctgacgaag cttcaggcac agaaccagtg gctgcaggac atggacactc atctcattct    60
gcgc                                                                 64
```

<210> SEQ ID NO 4
<211> LENGTH: 184
<212> TYPE: PRT
<213> ORGANISM: Artificial Sequence
<220> FEATURE:
<223> OTHER INFORMATION: Mutant IL-6 DFRD/D160R protein sequence

<400> SEQUENCE: 4

```
Pro Val Pro Pro Gly Glu Asp Ser Lys Asp Val Ala Ala Pro His Arg
1               5                   10                  15

Gln Pro Leu Thr Ser Ser Glu Arg Ile Asp Lys Gln Ile Arg Asp Ile
            20                  25                  30

Leu Asp Phe Ile Ser Ala Leu Arg Lys Glu Thr Cys Asn Lys Ser Asn
        35                  40                  45

Met Cys Glu Ser Ser Lys Glu Ala Leu Ala Glu Asn Asn Leu Asn Leu
50                  55                  60

Pro Lys Met Ala Glu Lys Asp Gly Cys Phe Gln Ser Gly Phe Asn Glu
65                  70                  75                  80

Glu Thr Cys Leu Val Lys Ile Ile Thr Gly Leu Leu Glu Phe Glu Val
                85                  90                  95

Tyr Leu Glu Tyr Leu Gln Asn Arg Phe Glu Ser Ser Glu Glu Gln Ala
            100                 105                 110

Arg Ala Val Gln Met Arg Thr Lys Asp Leu Ile Gln Phe Leu Gln Lys
        115                 120                 125

Lys Ala Lys Asn Leu Asp Ala Ile Thr Thr Pro Asp Pro Thr Thr Asn
130                 135                 140

Ala Ser Leu Leu Thr Lys Leu Gln Ala Gln Asn Gln Trp Leu Gln Asp
145                 150                 155                 160
```

Ile Thr Thr His Leu Ile Leu Arg Ser Phe Lys Glu Phe Leu Gln Ser
              165                 170                 175

Ser Leu Arg Ala Leu Arg Gln Met
              180

<210> SEQ ID NO 5
<211> LENGTH: 184
<212> TYPE: PRT
<213> ORGANISM: Artificial Sequence
<220> FEATURE:
<223> OTHER INFORMATION: Mutant IL-6 DFRD/W157R/D160R protein sequence

<400> SEQUENCE: 5

Pro Val Pro Pro Gly Glu Asp Ser Lys Asp Val Ala Ala Pro His Arg
1               5                   10                  15

Gln Pro Leu Thr Ser Ser Glu Arg Ile Asp Lys Gln Ile Arg Asp Ile
                20                  25                  30

Leu Asp Phe Ile Ser Ala Leu Arg Lys Glu Thr Cys Asn Lys Ser Asn
                35                  40                  45

Met Cys Glu Ser Ser Lys Glu Ala Leu Ala Glu Asn Asn Leu Asn Leu
        50                  55                  60

Pro Lys Met Ala Glu Lys Asp Gly Cys Phe Gln Ser Gly Phe Asn Glu
65                  70                  75                  80

Glu Thr Cys Leu Val Lys Ile Ile Thr Gly Leu Leu Glu Phe Glu Val
                85                  90                  95

Tyr Leu Glu Tyr Leu Gln Asn Arg Phe Glu Ser Ser Glu Glu Gln Ala
                100                 105                 110

Arg Ala Val Gln Met Arg Thr Lys Asp Leu Ile Gln Phe Leu Gln Lys
                115                 120                 125

Lys Ala Lys Asn Leu Asp Ala Ile Thr Thr Pro Asp Pro Thr Thr Asn
        130                 135                 140

Ala Ser Leu Leu Thr Lys Leu Gln Ala Gln Asn Gln Trp Leu Gln Asp
145                 150                 155                 160

Ile Thr Thr His Leu Ile Leu Arg Ser Phe Lys Glu Phe Leu Gln Ser
                165                 170                 175

Ser Leu Arg Ala Leu Arg Gln Met
                180

<210> SEQ ID NO 6
<211> LENGTH: 184
<212> TYPE: PRT
<213> ORGANISM: Artificial Sequence
<220> FEATURE:
<223> OTHER INFORMATION: Mutant IL-6 DFRD/T162D protein sequence

<400> SEQUENCE: 6

Pro Val Pro Pro Gly Glu Asp Ser Lys Asp Val Ala Ala Pro His Arg
1               5                   10                  15

Gln Pro Leu Thr Ser Ser Glu Arg Ile Asp Lys Gln Ile Arg Asp Ile
                20                  25                  30

Leu Asp Phe Ile Ser Ala Leu Arg Lys Glu Thr Cys Asn Lys Ser Asn
                35                  40                  45

Met Cys Glu Ser Ser Lys Glu Ala Leu Ala Glu Asn Asn Leu Asn Leu
        50                  55                  60

Pro Lys Met Ala Glu Lys Asp Gly Cys Phe Gln Ser Gly Phe Asn Glu
65                  70                  75                  80

Glu Thr Cys Leu Val Lys Ile Ile Thr Gly Leu Leu Glu Phe Glu Val
                85                  90                  95

```
Tyr Leu Glu Tyr Leu Gln Asn Arg Phe Glu Ser Ser Glu Glu Gln Ala
            100                 105                 110

Arg Ala Val Gln Met Arg Thr Lys Asp Leu Ile Gln Phe Leu Gln Lys
            115                 120                 125

Lys Ala Lys Asn Leu Asp Ala Ile Thr Thr Pro Asp Pro Thr Thr Asn
130                 135                 140

Ala Ser Leu Leu Thr Lys Leu Gln Ala Gln Asn Gln Trp Leu Gln Asp
145                 150                 155                 160

Ile Thr Thr His Leu Ile Leu Arg Ser Phe Lys Glu Phe Leu Gln Ser
            165                 170                 175

Ser Leu Arg Ala Leu Arg Gln Met
            180

<210> SEQ ID NO 7
<211> LENGTH: 184
<212> TYPE: PRT
<213> ORGANISM: Artificial Sequence
<220> FEATURE:
<223> OTHER INFORMATION: Sant 7 protein sequence
<220> FEATURE:
<221> NAME/KEY: misc_feature
<222> LOCATION: (175)..(175)
<223> OTHER INFORMATION: Xaa can be Thr or Ile

<400> SEQUENCE: 7

Pro Val Pro Pro Gly Glu Asp Ser Lys Asp Val Ala Ala Pro His Arg
1               5                   10                  15

Gln Pro Leu Thr Ser Ser Glu Arg Ile Asp Lys Gln Ile Arg Asp Ile
            20                  25                  30

Leu Asp Phe Ile Ser Ala Leu Arg Lys Glu Thr Cys Asn Lys Ser Asn
            35                  40                  45

Met Cys Glu Ser Ser Lys Glu Ala Asp Asp Phe Trp Asn Leu Asn Leu
            50                  55                  60

Pro Lys Met Ala Glu Lys Asp Gly Cys Phe Tyr Lys Gly Phe Asn Glu
65                  70                  75                  80

Glu Thr Cys Leu Val Lys Ile Ile Thr Gly Leu Phe Glu Phe Glu Val
            85                  90                  95

Tyr Leu Glu Tyr Leu Gln Asn Arg Phe Glu Ser Ser Glu Glu Gln Ala
            100                 105                 110

Arg Ala Val Gln Met Arg Thr Lys Asp Leu Ile Gln Phe Leu Gln Lys
            115                 120                 125

Lys Ala Lys Asn Leu Asp Ala Ile Thr Thr Pro Asp Pro Thr Thr Asn
130                 135                 140

Ala Ser Leu Leu Thr Lys Leu Gln Ala Gln Asn Gln Trp Leu Gln Asp
145                 150                 155                 160

Met Thr Thr His Leu Ile Leu Arg Ser Phe Lys Glu Phe Leu Xaa Arg
            165                 170                 175

Ser Leu Arg Ala Leu Arg Ala Met
            180

<210> SEQ ID NO 8
<211> LENGTH: 555
<212> TYPE: DNA
<213> ORGANISM: Homo sapiens
<220> FEATURE:
<221> NAME/KEY: CDS
<222> LOCATION: (1)..(555)
```

```
<400> SEQUENCE: 8 cca gta ccc cca gga gaa gat tcc aaa gat gta gcc gcc cca cac aga      48
Pro Val Pro Pro Gly Glu Asp Ser Lys Asp Val Ala Ala Pro His Arg
1               5                   10                  15 cag cca ctc acg agc tca gaa cga att gac aaa caa att cgg gac atc      96
Gln Pro Leu Thr Ser Ser Glu Arg Ile Asp Lys Gln Ile Arg Asp Ile
            20                  25                  30 ctc gac ttt atc tca gcc tta aga aag gag aca tgt aac aag agt aac     144
Leu Asp Phe Ile Ser Ala Leu Arg Lys Glu Thr Cys Asn Lys Ser Asn
        35                  40                  45 atg tgt gaa agc agc aaa gag gca ctg gca gaa aac aac ctg aac ctt     192
Met Cys Glu Ser Ser Lys Glu Ala Leu Ala Glu Asn Asn Leu Asn Leu
50                  55                  60 cca aag atg gct gaa aaa gat gga tgc ttc caa tct gga ttc aat gag     240
Pro Lys Met Ala Glu Lys Asp Gly Cys Phe Gln Ser Gly Phe Asn Glu
65                  70                  75                  80 gag act tgc ctg gtg aaa atc atc act ggt ctt ctc gag ttt gag gta     288
Glu Thr Cys Leu Val Lys Ile Ile Thr Gly Leu Leu Glu Phe Glu Val
                85                  90                  95 tac cta gag tac ctc cag aac aga ttt gag agt agt gag gaa caa gcc     336
Tyr Leu Glu Tyr Leu Gln Asn Arg Phe Glu Ser Ser Glu Glu Gln Ala
            100                 105                 110 aga gct gtc cag atg cgc aca aaa gac ctg atc cag ttc ctg cag aaa     384
Arg Ala Val Gln Met Arg Thr Lys Asp Leu Ile Gln Phe Leu Gln Lys
        115                 120                 125 aag gca aag aat cta gat gca ata acc acc cct gac cca acc aca aat     432
Lys Ala Lys Asn Leu Asp Ala Ile Thr Thr Pro Asp Pro Thr Thr Asn
130                 135                 140 gcc agc ctg ctg acg aag ctt cag gca cag aac cag tgg ctg cag gac     480
Ala Ser Leu Leu Thr Lys Leu Gln Ala Gln Asn Gln Trp Leu Gln Asp
145                 150                 155                 160 ata aca act cat ctc att ctg cgc agc ttt aag gag ttc ctg cag tcc     528
Ile Thr Thr His Leu Ile Leu Arg Ser Phe Lys Glu Phe Leu Gln Ser
                165                 170                 175 agc ctg agg gct ctt cgg caa atg tag                                 555
Ser Leu Arg Ala Leu Arg Gln Met
                180

<210> SEQ ID NO 9
<211> LENGTH: 555
<212> TYPE: DNA
<213> ORGANISM: Artificial Sequence
<220> FEATURE:
<223> OTHER INFORMATION: Mutant IL-6 DFRD/D160R DNA sequence
<220> FEATURE:
<221> NAME/KEY: CDS
<222> LOCATION: (1)..(555)

<400> SEQUENCE: 9 cca gta ccc cca gga gaa gat tcc aaa gat gta gcc gcc cca cac aga      48
Pro Val Pro Pro Gly Glu Asp Ser Lys Asp Val Ala Ala Pro His Arg
1               5                   10                  15 cag cca ctc acg agc tca gaa cga att gac aaa caa att cgg gac atc      96
Gln Pro Leu Thr Ser Ser Glu Arg Ile Asp Lys Gln Ile Arg Asp Ile
            20                  25                  30 ctc gac ttt atc tca gcc tta aga aag gag aca tgt aac aag agt aac     144
Leu Asp Phe Ile Ser Ala Leu Arg Lys Glu Thr Cys Asn Lys Ser Asn
        35                  40                  45 atg tgt gaa agc agc aaa gag gca ctg gca gaa aac aac ctg aac ctt     192
Met Cys Glu Ser Ser Lys Glu Ala Leu Ala Glu Asn Asn Leu Asn Leu
50                  55                  60
```

-continued

| | |
|---|---|
| cca aag atg gct gaa aaa gat gga tgc ttc caa tct gga ttc aat gag<br>Pro Lys Met Ala Glu Lys Asp Gly Cys Phe Gln Ser Gly Phe Asn Glu<br>65                    70                        75                        80 | 240 |
| gag act tgc ctg gtg aaa atc atc act ggt ctt ctc gag ttt gag gta<br>Glu Thr Cys Leu Val Lys Ile Ile Thr Gly Leu Leu Glu Phe Glu Val<br>                        85                        90                        95 | 288 |
| tac cta gag tac ctc cag aac aga ttt gag agt agt gag gaa caa gcc<br>Tyr Leu Glu Tyr Leu Gln Asn Arg Phe Glu Ser Ser Glu Glu Gln Ala<br>                      100                        105                      110 | 336 |
| aga gct gtc cag atg cgc aca aaa gac ctg atc cag ttc ctg cag aaa<br>Arg Ala Val Gln Met Arg Thr Lys Asp Leu Ile Gln Phe Leu Gln Lys<br>                115                        120                      125 | 384 |
| aag gca aag aat cta gat gca ata acc acc cct gac cca acc aca aat<br>Lys Ala Lys Asn Leu Asp Ala Ile Thr Thr Pro Asp Pro Thr Thr Asn<br>130                    135                        140 | 432 |
| gcc agc ctg ctg acg aag ctt cag gca cag aac cag tgg ctg cag gac<br>Ala Ser Leu Leu Thr Lys Leu Gln Ala Gln Asn Gln Trp Leu Gln Asp<br>145                    150                        155                      160 | 480 |
| ata aca act cat ctc att ctg cgc agc ttt aag gag ttc ctg cag tcc<br>Ile Thr Thr His Leu Ile Leu Arg Ser Phe Lys Glu Phe Leu Gln Ser<br>                        165                        170                      175 | 528 |
| agc ctg agg gct ctt cgg caa atg tag<br>Ser Leu Arg Ala Leu Arg Gln Met<br>                180 | 555 |

<210> SEQ ID NO 10
<211> LENGTH: 555
<212> TYPE: DNA
<213> ORGANISM: Artificial Sequence
<220> FEATURE:
<223> OTHER INFORMATION: Mutant IL-6 DFRD/W157R/D160R DNA sequence
<220> FEATURE:
<221> NAME/KEY: CDS
<222> LOCATION: (1)..(555)

<400> SEQUENCE: 10

| | |
|---|---|
| cca gta ccc cca gga gaa gat tcc aaa gat gta gcc gcc cca cac aga<br>Pro Val Pro Pro Gly Glu Asp Ser Lys Asp Val Ala Ala Pro His Arg<br>1                    5                        10                        15 | 48 |
| cag cca ctc acg agc tca gaa cga att gac aaa caa att cgg gac atc<br>Gln Pro Leu Thr Ser Ser Glu Arg Ile Asp Lys Gln Ile Arg Asp Ile<br>                    20                        25                      30 | 96 |
| ctc gac ttt atc tca gcc tta aga aag gag aca tgt aac aag agt aac<br>Leu Asp Phe Ile Ser Ala Leu Arg Lys Glu Thr Cys Asn Lys Ser Asn<br>                        35                        40                      45 | 144 |
| atg tgt gaa agc agc aaa gag gca ctg gca gaa aac aac ctg aac ctt<br>Met Cys Glu Ser Ser Lys Glu Ala Leu Ala Glu Asn Asn Leu Asn Leu<br>50                      55                        60 | 192 |
| cca aag atg gct gaa aaa gat gga tgc ttc caa tct gga ttc aat gag<br>Pro Lys Met Ala Glu Lys Asp Gly Cys Phe Gln Ser Gly Phe Asn Glu<br>65                      70                        75                        80 | 240 |
| gag act tgc ctg gtg aaa atc atc act ggt ctt ctc gag ttt gag gta<br>Glu Thr Cys Leu Val Lys Ile Ile Thr Gly Leu Leu Glu Phe Glu Val<br>                        85                        90                        95 | 288 |
| tac cta gag tac ctc cag aac aga ttt gag agt agt gag gaa caa gcc<br>Tyr Leu Glu Tyr Leu Gln Asn Arg Phe Glu Ser Ser Glu Glu Gln Ala<br>                      100                        105                      110 | 336 |
| aga gct gtc cag atg cgc aca aaa gac ctg atc cag ttc ctg cag aaa<br>Arg Ala Val Gln Met Arg Thr Lys Asp Leu Ile Gln Phe Leu Gln Lys<br>                115                        120                      125 | 384 |

```
aag gca aag aat cta gat gca ata acc acc cct gac cca acc aca aat      432
Lys Ala Lys Asn Leu Asp Ala Ile Thr Thr Pro Asp Pro Thr Thr Asn
    130                 135                 140 gcc agc ctg ctg acg aag ctt cag gca cag aac cag tgg ctg cag gac      480
Ala Ser Leu Leu Thr Lys Leu Gln Ala Gln Asn Gln Trp Leu Gln Asp
145                 150                 155                 160 ata aca act cat ctc att ctg cgc agc ttt aag gag ttc ctg cag tcc      528
Ile Thr Thr His Leu Ile Leu Arg Ser Phe Lys Glu Phe Leu Gln Ser
                165                 170                 175 agc ctg agg gct ctt cgg caa atg tag                                  555
Ser Leu Arg Ala Leu Arg Gln Met
            180

<210> SEQ ID NO 11
<211> LENGTH: 555
<212> TYPE: DNA
<213> ORGANISM: Artificial Sequence
<220> FEATURE:
<223> OTHER INFORMATION: Mutant IL-6 DFRD/T162D DNA sequence
<220> FEATURE:
<221> NAME/KEY: CDS
<222> LOCATION: (1)..(555)

<400> SEQUENCE: 11 cca gta ccc cca gga gaa gat tcc aaa gat gta gcc gcc cca cac aga       48
Pro Val Pro Pro Gly Glu Asp Ser Lys Asp Val Ala Ala Pro His Arg
1               5                   10                  15 cag cca ctc acg agc tca gaa cga att gac aaa caa att cgg gac atc       96
Gln Pro Leu Thr Ser Ser Glu Arg Ile Asp Lys Gln Ile Arg Asp Ile
            20                  25                  30 ctc gac ttt atc tca gcc tta aga aag gag aca tgt aac aag agt aac      144
Leu Asp Phe Ile Ser Ala Leu Arg Lys Glu Thr Cys Asn Lys Ser Asn
        35                  40                  45 atg tgt gaa agc agc aaa gag gca ctg gca gaa aac aac ctg aac ctt      192
Met Cys Glu Ser Ser Lys Glu Ala Leu Ala Glu Asn Asn Leu Asn Leu
50                  55                  60 cca aag atg gct gaa aaa gat gga tgc ttc caa tct gga ttc aat gag      240
Pro Lys Met Ala Glu Lys Asp Gly Cys Phe Gln Ser Gly Phe Asn Glu
65                  70                  75                  80 gag act tgc ctg gtg aaa atc atc act ggt ctt ctc gag ttt gag gta      288
Glu Thr Cys Leu Val Lys Ile Ile Thr Gly Leu Leu Glu Phe Glu Val
                85                  90                  95 tac cta gag tac ctc cag aac aga ttt gag agt agt gag gaa caa gcc      336
Tyr Leu Glu Tyr Leu Gln Asn Arg Phe Glu Ser Ser Glu Glu Gln Ala
            100                 105                 110 aga gct gtc cag atg cgc aca aaa gac ctg atc cag ttc ctg cag aaa      384
Arg Ala Val Gln Met Arg Thr Lys Asp Leu Ile Gln Phe Leu Gln Lys
        115                 120                 125 aag gca aag aat cta gat gca ata acc acc cct gac cca acc aca aat      432
Lys Ala Lys Asn Leu Asp Ala Ile Thr Thr Pro Asp Pro Thr Thr Asn
    130                 135                 140 gcc agc ctg ctg acg aag ctt cag gca cag aac cag tgg ctg cag gac      480
Ala Ser Leu Leu Thr Lys Leu Gln Ala Gln Asn Gln Trp Leu Gln Asp
145                 150                 155                 160 ata aca act cat ctc att ctg cgc agc ttt aag gag ttc ctg cag tcc      528
Ile Thr Thr His Leu Ile Leu Arg Ser Phe Lys Glu Phe Leu Gln Ser
                165                 170                 175 agc ctg agg gct ctt cgg caa atg tag                                  555
Ser Leu Arg Ala Leu Arg Gln Met
            180
```

-continued

```
<210> SEQ ID NO 12
<211> LENGTH: 555
<212> TYPE: DNA
<213> ORGANISM: Artificial Sequence
<220> FEATURE:
<223> OTHER INFORMATION: Sant 7 DNA sequence
<220> FEATURE:
<221> NAME/KEY: CDS
<222> LOCATION: (1)..(555)

<400> SEQUENCE: 12 cca gta ccc cca gga gaa gat tcc aaa gat gta gcc gcc cca cac aga      48
Pro Val Pro Pro Gly Glu Asp Ser Lys Asp Val Ala Ala Pro His Arg
1               5                  10                  15 cag cca ctc acg agc tca gaa cga att gac aaa caa att cgg gac atc      96
Gln Pro Leu Thr Ser Ser Glu Arg Ile Asp Lys Gln Ile Arg Asp Ile
            20                  25                  30 ctc gac ttt atc tca gcc tta aga aag gag aca tgt aac aag agt aac     144
Leu Asp Phe Ile Ser Ala Leu Arg Lys Glu Thr Cys Asn Lys Ser Asn
        35                  40                  45 atg tgt gaa agc agc aaa gag gcc gac gac ttc tgg aac ctg aac ctt     192
Met Cys Glu Ser Ser Lys Glu Ala Asp Asp Phe Trp Asn Leu Asn Leu
    50                  55                  60 cca aag atg gct gaa aaa gac gga tgc ttc tac aaa gga ttc aat gag     240
Pro Lys Met Ala Glu Lys Asp Gly Cys Phe Tyr Lys Gly Phe Asn Glu
65                  70                  75                  80 gag act tgc ctg gtg aaa atc atc act ggt ctt ttc gag ttt gag gta     288
Glu Thr Cys Leu Val Lys Ile Ile Thr Gly Leu Phe Glu Phe Glu Val
                85                  90                  95 tac cta gag tac ctc cag aac aga ttt gag agt agt gag gaa caa gcc     336
Tyr Leu Glu Tyr Leu Gln Asn Arg Phe Glu Ser Ser Glu Glu Gln Ala
            100                 105                 110 aga gct gtc cag atg cgc aca aaa gac ctg atc cag ttc ctg cag aaa     384
Arg Ala Val Gln Met Arg Thr Lys Asp Leu Ile Gln Phe Leu Gln Lys
        115                 120                 125 aag gca aag aat cta gat gca ata acc acc cct gac cca acc aca aat     432
Lys Ala Lys Asn Leu Asp Ala Ile Thr Thr Pro Asp Pro Thr Thr Asn
    130                 135                 140 gcc agc ctg ctg acg aag ctg cag gca cag aac cag tgg ctg cag gac     480
Ala Ser Leu Leu Thr Lys Leu Gln Ala Gln Asn Gln Trp Leu Gln Asp
145                 150                 155                 160 atg aca act cat ctc att ctg cgc agc ttt aag gag ttc ctg ayc cgt     528
Met Thr Thr His Leu Ile Leu Arg Ser Phe Lys Glu Phe Leu Xaa Arg
                165                 170                 175 agc ctg agg gct ctt cgg gct atg tag                                 555
Ser Leu Arg Ala Leu Arg Ala Met
            180
```

USE OF INTERLEUKIN-6 ANTAGONISTS FOR THE TREATMENT OF DISEASES CHARACTERIZED BY HIGH LEVELS OF AROMATASE

This application is a divisional of application Ser. No. 10/220,183, filed Nov. 27, 2002 now abandoned; which is a national phase application of Int'l Patent Appln. No. PCT/IT00/00072 filed Mar. 6, 2000, the entire contents of which are hereby incorporated by reference in this application.

The invention described herein relates to the use of interleukin-6 (IL-6) antagonists for the preparation of a medicinal agent for the treatment of diseases presenting high aromatase levels.

Aromatase is a regulatory enzyme in oestrogen synthesis.

Oestrogens are known to play a central role in the growth of breast tumours in a hormone-dependent manner (James V H T, Reed M J; Prog Cancer Res Ther 1980, 14:471–487).

It has been found, however, that the highest incidence of breast tumours develops in postmenopausal women, i.e. at a time when the ovaries have stopped producing oestrogens. The greater frequency of breast tumours precisely during the period when oestrogen production has ceased, and therefore when the tumour risk should be lower, is only apparently paradoxical. In actual fact, the enzymes necessary for the peripheral synthesis of oestrogens are also present in other body tissues, such as adipose and mammary tissue (James V H T, McNeill J M, Lai L C, Newton C J, Ghilchik M V, Reed M J; 1987, 50:269–279).

Cytokines are important regulators in oestrogen synthesis in normal or cancerous mammary tissue (Reed M J, Purohit A, Endocrine Review 18(5): 701–715).

The peripheral synthesis of oestrogens derives mainly from the activity of three enzymes, namely, aromatase, oestrone sulphatase or sulphotransferase), and oestradiol dehydrogenase (Type I) (E2DH).

The first of these enzyme complexes, aromatase, converts adrenocortical androstenedione to oestrone and is widely distributed in muscular and adipose tissue (Longcope C, Pratt J H, Schneider S H, Fineberg S E, 1977, J. Clin. Endocrinol. Metab. 45:1134–1145). Aromatase activity is also detectable in normal mammary tissue and in 40–50% of cancerous mammaxy tissue.

The increased conversion of androstenedione to oestrone associated with obesity increases the risk of such subjects developing a hormone-dependent tumour (De Waard F W, 1975 Cancer Res. 35: 3351–3356).

An increase in aromatase activity occurring concomitantly with ageing, as observed in in-vivo studies, has been confirmed in a further study in which aromatase activity in adipose tissue is measured in vitro (Cleland W H, Mendelson C R, Simpson E R, 1985 J. Clin. Endocrinol. Metab. 60:174–177).

Results of in-vitro and in-vivo experiments have demonstrated that, in tumours of the breast, oestrone is preferably converted to oestradiol and that aromatase activity is greater than in normal mammary tissue (James V H T, McNeill J M, Lai L C, Newton C J, Ghilchik M V, Reed M J; 1987, 50:269–279).

The second enzyme, oestrone sulphatase, permits the conversion of oestrone, obtained by means of the above-mentioned aromatase activity, to oestrone sulphate (Reed M J, Purohit A 1993, Rev. Endocr. Relat. Cancer 45:51–62).

This hormone has been found to be associated with hormone-dependent tumours (Masamura S, Santner S J, Santen R J, 1996, J. Steroid Biochem. Mol. Biol 58:425–430).

The third enzyme, E2DH, permits the conversion of oestrone, formed both from androstenedione and from oestrone sulphate, to oestradiol and has been found to be associated with breast cancer (McNeill J M, Reed M J; Beranek P A; Bonney R C; Gbilchik M V; Robinson D J, James V H T; 1986 Int. J. Cancer 38:193–196).

Cytokines, particularly IL-6 and Tumor Necrosis Factor-α (TNF-α), play a crucial role in the regulation of oestrogen synthesis in breast cancer cells. Both IL 6 and TNF-α stimulate aromatase activity, E2DH activity, and oestrone sulphatase activity, and, in addition, are capable of acting synergistically to increase the activity of these enzymes.

Whereas part of the Il-6 is secreted by fibroblasts deriving from breast cancer cells, most of the IL-6 produced derives from lymphocytes and macrophages infiltrating the tumour mass. In fact, 50% of the volume of a breast tumour consists of macrophages and lymphocytes.

The ability of Il-6 to stimulate aromatase activity may be markedly reinforced (20- to 40-fold) by the Il-6 soluble receptor (IL-6 sR).

Il-6 sR is produced by malignant epithelial cells, tumour-derived fibroblasts and, particularly, tumour-associated macrophages (TAMs) and tumour-infiltrating lymphocytes (TILs), but not by normal stromal cells. The production of IL-6 sR by tumour cells is increased by oestradiol.

The interleukin-6 receptor (IL-6 R) and/or IL-6 soluble receptor can interact with the gp130 protein component of the IL-6 R system. This interaction is required for the induction of the transduction signal deriving from IL-6 bound to its receptor.

TNF-α secreted by adipocytes and by cells of the immune system increases the expression of the gp130 protein component of the IL-6 R signalling system, giving rise to a synergistic effect of IL-6 and TNF-α in stimulating the production of oestrogen synthesis. The complex oestrogen synthesis regulation system in breast tumours is extensively co-ordinated by cytokines. The result of the co-ordinated stimulation of oestrogen synthesis is the cause of the high oestradiol concentrations found in breast cancer (Reed M J, Purohit A, Endocrine Review 18(5): 701–715).

Breast cyst fluids (BCFs) stimulate aromatase and E2DH activity in breast cells cultured in vitro (such cysts are present in many premenopausal women and are associated with an increase in occurrence of breast cancer).

BCFs subjected to radioimmunoassay (RIA) analysis have shown the presence of cytokines IL-1 and IL-6, and both these cytokines are capable of stimulating aromatase activity in fibroblasts deriving from breast cancer cells Duncan L. J., Robinson G. V., Ghilchik M. V., Reed M. J., 1994 Endocr. Relat. Cancer 2:27–35; Reed M. J., Coldham N. J., Patel S. R., Ghilchik M. W., James V. H. T., 1992, J. Endocrinol. 132:R5–R8).

In the first study regarding aromatase activity in vivo, it was noted that dexamethasone markedly stimulates aromatse activity in the presence of fetal calf serum (FCS) (Simpson E. R., Merril J. C., Hollub A. J., Graham-Lorence S., Mendelson C. R., 1989 Endocr. Rev. 10:136–148).

It has been found that the IL-6 concentration in BCFs is 1000-fold greater than the IL-1 concentration in the same fluids and that IL-6 is the main aromatase activity stimulating factor in BCFs. Compounds inhibiting aromatase activity are already known and can be divided into two groups, called non-steroidal inhibitors and steroidal inhibitors, respectively.

Aminogluthetimide is a non-steroidal aromatase inhibitor and has long been used for the treatment of breast cancer. The inhibition of aromatase activity by aminogluthetimide is not selective; this compound, in fact, also inhibits other enzymes involved in the metabolic pathway of steroidogenesis and is therefore not easily utilisable because of its toxicity (Oncologist 1998; 3(2):129–130).

Anastrazole is a non-steroidal aromatase inhibitor. This compound is not devoid of drawbacks and, in fact, presents the disadvantage of causing gastrointestinal disorders in patients treated with it (Cancer 1997 Feb. 15;79(4):730–9).

Letrozole is a non-steroidal aromatase inhibitor capable of reducing aromatase activity only by 5–10% compared to basal levels (Recent Results Cancer Res. 1998; 152:227–84).

Formestane is a steroidal aromatase inhibitor. it is less toxic than aminogluthetimide, but presents the drawback that it can be administered only intramuscularly (Oncology (Huntingt) 1997 Nov; 11(11):1697–703).

Exemestane is a steroidal aromatase inhibitor. This compound is not devoid of drawbacks. In fact, it causes headache in 45% of treated patients, dizziness in 33%, nausea in 33%, and other side effects (Anticancer Drugs 1998 Sept; 9(8): 675–83).

In WO 98/15283, an amino acid sequence composed of 16 amino acids is described, which is capable of inhibiting aromatase activity by 67% compared to basal levels.

Other aromatase activity inhibitors are also known.

A great deal of effort has been made and continues to be made in the field of aromatase inhibitors aimed at the treatment of hormone-dependent tumours, particularly cancer of the breast. In fact, there is still a strongly perceived need to find new, increasingly specific aromatase inhibitors which are capable of affording greater inhibition of aromatase activity and are devoid of the unwanted side effects of the above-mentioned known compounds.

It has now been found—and this is the subject of the invention described herein—that a series of antagonists of human interleukin-6, totally incapable of binding to gp130, are specific, potent inhibitors of the enzyme aromatase.

The compounds according to the invention have the following amino acid sequences: SEQ ID NO: 1, SEQ ID NO: 4, SEQ ID NO: 5, SEQ ID NO: 6, and SEQ ID NO: 7 (Sant 7). They are encoded by the following nucleotide sequences: SEQ ID NO: 8, SEQ ID NO: 9, SEQ ID NO: 10, SEQ ID NO: 11, and SEQ ID NO: 12; respectively.

The compounds according to the invention were first described in WO 96/34104.

WO 96/34104 tells us that these compounds are human interleukin-6 antagonists totally incapable of binding to gp130 and that they are useful agents for the treatment of multiple myeloma, rheumatoid arthritis, systemic lupus erythematosus, and osteoporosis.

In WO 96/34104, these compounds are not described as, or claimed to be, useful agents for the treatment of diseases caused by increased aromatase activity, or for the treatment of hormone-dependent tumours.

The compounds described in WO 96/34104 have completely different amino acid sequences from the one described in WO 98/15283 mentioned above.

The applicant has found that the compounds according to the invention possess a substantial ability to inhibit aromatase activity in a highly specific manner as compared to the known compounds and that they can be usefully applied therapeutically in the treatment of hormone-dependent tumours, particularly cancer of the breast.

These compounds have a potent inhibitory effect on the enzyme aromatase and an inhibitory effect both on the enzymes oestrone sulphatase and E2DH. In this way, the oestrone produced by androstenedione, by means of aromatase activity, is no longer available and thus cannot be converted to oestrone sulphate by means of oestrone sulphatase activity. Consequently, as a result of the shortage of oestrone, the oestradiol dehydrogenase activity of E2DH is inhibited with inhibition of the production of oestradiol.

As previously mentioned, the peripheral synthesis of oestrogens derives mainly from the activity of three enzymes, namely, aromatase, oestrone sulphatase and oestradiol dehydrogenase (E2DH). Aromatase converts corticoadrenal androstenedione to oestrone. In breast tumours, oestrone is converted to oestradiol and aromatase activity is greater in tumour tissue than in normal mammary tissue. Oestrone sulphotransferase permits the conversion of oestrone, obtained by means of the above-mentioned aromatase activity, to oestrone sulphate, and oestrone sulphate is associated with hormone-dependent tumours. Lastly, E2DH allows the conversion of oestrone, formed both from androstenedione and from oestrone sulphate, to oestradiol and oestradiol is associated with breast cancer.

The compounds according to the invention possess a substantial capacity to inhibit aromatase activity and can be usefully applied therapeutically in the treatment of hormone-dependent tumours, particularly tumours of the breast. Moreover, such compounds are also useful agents for the prevention of onset of breast cancer.

In fact, subjects at high risk of breast cancer, such as, for instance, obese persons and/or subjects with precancerous nodules (breast cysts) can be treated with the compounds according to the invention for the prevention of such diseases.

The subject of the invention described herein is therefore the use of compounds with an amino acid sequence selected from the group consisting of SEQ ID NO: 1, SEQ ID NO: 4, SEQ ID NO: 5, SEQ ID NO: 6, and SEQ ID NO: 7 (Sant 7) for the preparation of a medicinal agent for the prevention or treatment of diseases mediated by an increase in aromatase activity.

Among the compounds according to the invention the one preferred is Sant 7. A further subject of the invention described herein is the use of an amino acid sequence selected from the group consisting of SEQ ID NO: 1, SEQ ID NO: 4, SEQ ID NO: 5, SEQ ID NO: 6, and SEQ ID NO: 7, for the preparation of a medicinal agent for the prevention or treatment of oestrogen-dependent tumours.

A further subject of the invention described herein is the use of an amino acid sequence selected from the group consisting of SEQ ID NO: 1, SEQ ID NO: 4, SEQ ID NO: 5, SEQ ID NO: 6, and SEQ ID NO: 7, for the preparation of a medicinal agent for the prevention or treatment of breast tumours.

A further subject of the invention described herein is the use of an amino acid sequence selected from the group consisting of SEQ ID NO: 1, SEQ ID NO: 2, SEQ ID NO: 3, SEQ ID NO: 4, SEQ ID NO: 5, SEQ ID NO: 6, and SEQ ID NO: 7, for the preparation of a medicinal agent endowed with antioestrogen activity.

A further subject of the invention described herein is the use of an amino acid sequence selected from the group consisting of SEQ ID NO: 1, SEQ ID NO: 4, SEQ ID NO: 5, SEQ ID NO: 6, and SEQ ID NO: 7, for the preparation of a medicinal agent with an inhibitory effect on oestrogen synthesis, in which the enzyme catalyzing oestrogen synthesis is selected from the group consisting of aromatase, oesterone sulphatase and oestradiol dehydrogenase.

A further subject of the invention described herein is the use of a fragment of a compound selected from the group consisting of SEQ ID NO: 1, SEQ ID NO: 4, SEQ ID NO:

5, SEQ ID NO: 6, and SEQ ID NO: 7, which conserves the activity of the sequence it derives from, for the preparation of a medicinal agent useful for the prevention or treatment of diseases mediated by an increase in aromatase activity.

A further subject of the invention described herein is the use of a fragment of a compound selected from the group consisting of SEQ ID NO: 1, SEQ ID NO: 4, SEQ ID NO: 5, SEQ ID NO: 6, and SEQ ID NO: 7, which conserves the activity of the sequence it derives from, for the preparation of a medicinal agent useful for the prevention or treatment of oestrogen-dependent tumours.

A further subject of the invention described herein is the use of a fragment of a compound selected from the group consisting of SEQ ID NO: 1, SEQ ID NO: 4, SEQ ID NO: 5, SEQ ID NO: 6, and SEQ ID NO: 7, for the prevention or treatment of breast tumours.

A further subject of the invention described herein is the use of a fragment of a compound selected from the group consisting of SEQ ID NO: 1, SEQ ID NO: 4, SEQ ID NO: 5, SEQ ID NO: 6, and SEQ ID NO: 7, which conserves the activity of the sequence it derives from, for the preparation of a medicinal agent endowed with antioestrogen activity.

A further subject of the invention described herein is the use of a fragment of a compound selected from the group consisting of SEQ ID NO: 1, SEQ ID NO: 4, SEQ ID NO: 5, SEQ ID NO: 6, and SEQ ID NO: 7, which conserves the activity of the sequence it derives from, for the preparation of a medicinal agent with an inhibitory effect on oestrogen synthesis, in which the enzyme catalyzing oestrogen synthesis is selected from the group consisting of aromatase, oesterone sulphatase, and oestradiol dehydrogenase.

The compounds according to the invention can be administered alone or in combination with one or more pharmacologically acceptable diluents and/or vehicles and with one or more therapeutic agents, and/or antioxidants, and/or vitamins and with other agents useful for support therapy compatible with the compound itself.

The compounds according to the invention can be suitably administered orally, via oral inhalation or via intranasal inhalation; parenterally, including subcutaneous, transdermal, intradermal, intramuscular and intravenous administration; or rectally.

The formulations according to the invention described herein, suitable for oral administration and prepared on the basis of methods known to pharmaceutical technology, may be in the form of capsules, sachets, granules or powders, tablets containing a predetermined amount of active ingredient; or in the form of aqueous or non-aqueous liquid suspensions; or in the form of emulsions; liposomes; or in spray form with a metered-dose inhaler.

The formulations for parenteral administration include sterile and non-sterile aqueous solutions, which may contain antioxidants, buffers, bacteriostatic agents and/or solutes which make the formulation isotonic; or in lyophilised form. These formulations may also include suspending and/or disaggregating agents.

The formulations for parenteral administration may be contained in ampoules or vials containing a sterile liquid, or a sterile powder to be reconstituted, for the preparation of an extempore injectable solution.

A number of experimental results further illustrating the invention are described here below.

EXAMPLE 1

In this experiment, for the purposes of evaluating the inhibition of aromatase activity, fibroblasts derived from mammary tissue of women undergoing reductive mastectomy were used.

Aromatase activity was evaluated in primary cultures of these fibroblasts according to the following procedure.

Cells were grown to 80% confluence and then washed with Earle's balanced salt solution (5 mL) and cultured for 24 hours in phenol red-free Eagle's minimum essential medium added with 2% fetal calf serum (FCS) and in the presence of 100 nM of dexamethasone (Dex).

As previously mentioned, dexamethasone, markedly stimulates aromatase activity in vitro in the presence of fetal calf serum. Culture medium containing IL-6 (50 ng/mL); or IL-6 sR (100 ng/mL); or Sant 7 (10 μg/mL); or IL-6 plus IL-6 sR; or IL-6 plus Sant 7; or IL-6 plus IL-6 sR plus Sant 7 was then added.

Cells were incubated for a further 48 hours.

Aromatase activity was evaluated on a single layer of cells by measuring the production of $^3H_2O$ by [1β-$^3$H] androstenedione (15–30 Ci/mmol).

Figure 1:
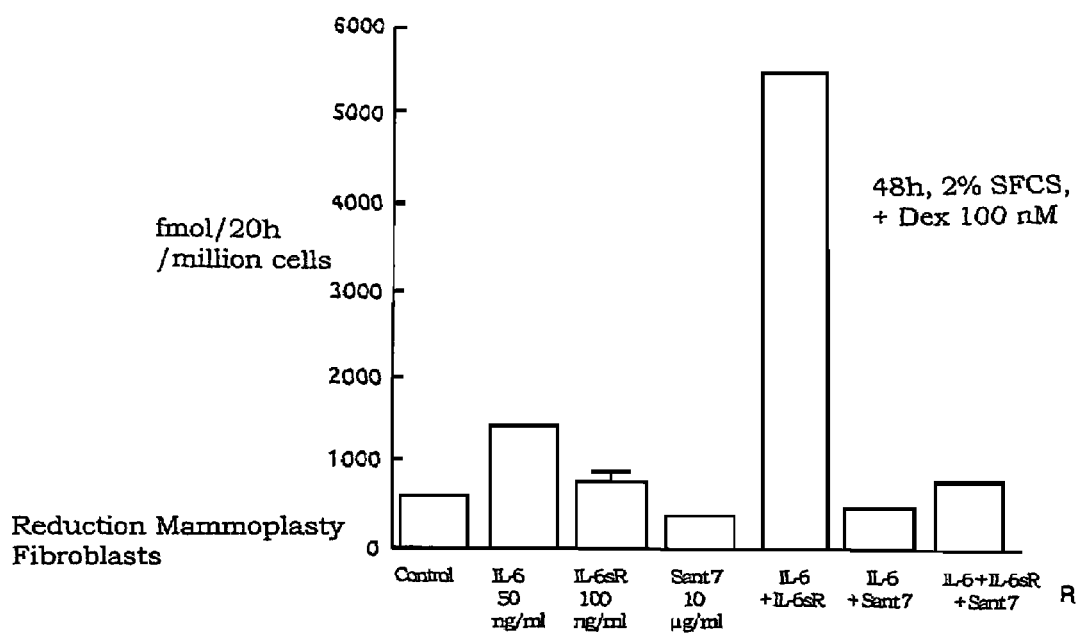
FIG. 1 shows aromatase activity in a primary culture of fibroblasts derived from mammary tissue of women undergoing reductive mastectomy.

The results obtained are reported in FIG. 1.

EXAMPLE 2

In this experiment, for the purposes of evaluating the inhibition of aromatase activity, fibroblasts derived from normal tissue proximal to tumour tissue (NFS) were used.

Aromatase activity was evaluated in primary cultures of these fibroblasts according to the following procedure.

Cells were grown to 80% confluence and then washed with Earle's balanced salt solution (5 mL) and cultured for 24 hours in phenol red-free Eagle's minimum essential medium added with 2% fetal calf serum and in the presence of 100 nM of dexamethasone.

Culture medium was then added containing IL-6 (50 ng/mL); or IL-6 sR (100 ng/mL); or Sant 7 (10 μg/mL); or IL-6 plus IL-6 sR; or IL-6 plus IL-6 sR plus Sant 7, the last of these being added 3 hours before IL-6 plus IL-6 sR, i.e. with three hours' pretreatment with Sant 7; or IL-6 plus IL-6 sR plus Sant 7 without pretreatment.

Cells were incubated for a further 48 hours.

Aromatase activity was evaluated on a single layer of cells by measuring the production of $^3H_2O$ by [1β-$^3$H] androstenedione (15–30 Ci/mmol).

Figure 2:
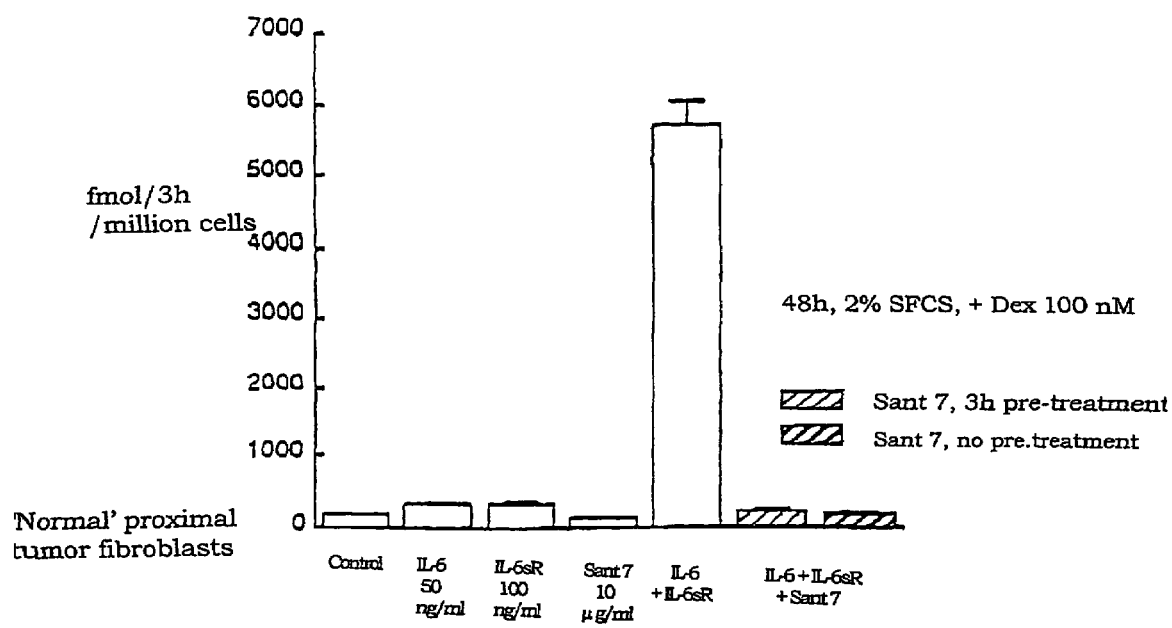
FIG. 2 shows aromatase activity in a primary culture of fibroblasts derived from normal tissue proximal to tumour tissue.

The results obtained are reported in FIG. 2.

EXAMPLE 3

In this experiment, for the purposes of evaluating the inhibition of aromatase activity, fibroblasts derived from breast tumours were used (TFs).

Aromatase activity was evaluated in primary cultures of these fibroblasts according to the following procedure.

Cells were grown to 80% confluence and then washed with Earle's balanced salt solution (5 mL) and cultured for 24 hours in phenol red-free Eagle's minimum essential medium added with 2% fetal calf serum and in the presence of 100 nM of dexamethasone.

Culture medium containing IL-6 (50 ng/mL); or IL-6 (50 ng/mL) plus IL-6 sR (100 ng/mL); or Sant 7 (10 μg/mL); or IL-6 plus IL-6 sR plus Sant 7 was then added.

Cells were incubated for a further 48 hours.

Aromatase activity was evaluated on a single layer of cells by measuring the production of $^3H_2O$ by [1β-$^3$H] androstenedione (15–30 Ci/mmol).

Figure 3:
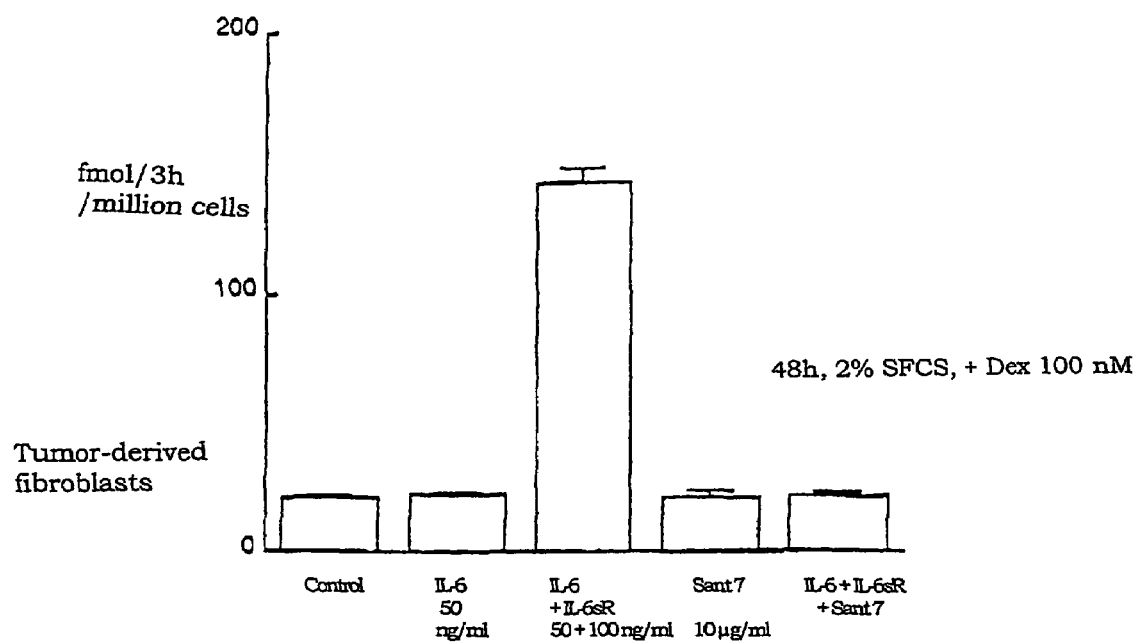
FIG. 3 shows aromatase activity in a primary culture of fibroblasts derived from breast tumours.

The results obtained are reported in FIG. 3.

EXAMPLE 4

In this experiment, for the purposes of evaluating the dose-response effect of Sant 7 on inhibition of aromatase activity, fibroblasts derived from normal tissue proximal to tumour tissue (NFS) were used.

Aromatase activity was evaluated in primary cultures of these fibroblasts according to the following procedure.

Cells were grown to 80% confluence and then washed with Earle's balanced salt solution (5 mL) and cultured for 24 hours in phenol red-free Eagle's minimum essential medium added with 2% fetal calf serum and in the presence of 100 nM of dexamethasone.

Culture medium was then added containing IL-6 (50 ng/mL) plus IL-6 sR (100 ng/mL); or IL-6 (50 ng/mL) plus IL-6 sR (100 ng/mL) plus Sant 7 at doses of 0.1, 0.5, 1.0, 5.0, or 10 μg/mL, respectively.

Cells were incubated for a further 48 hours.

Aromatase activity was evaluated on a single layer of cells by measuring the production of $^3H_2O$ by [1β-$^3$H] androstenedione (15–30 Ci/mmol).

Figure 4:
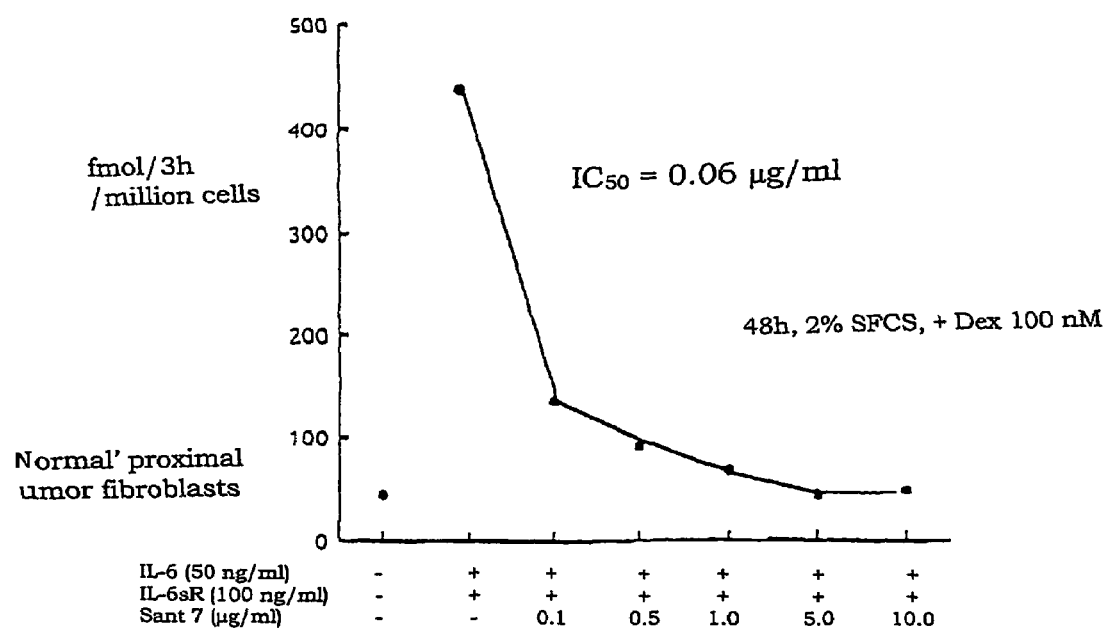
FIG. 4 shows aromatase activity in a primary culture of fibroblasts derived from normal tissue proximal to tumour tissue. The inhibitory effect is dose dependent.

The results obtained are reported in FIG. 4.

RESULTS

The results reported in FIGS. 1, 2 and 3 show that IL-6 plus IL-6 sR markedly stimulate aromatase activity.

In FIGS. 1 and 2, it can be noted that Sant 7 alone was capable of reducing basal aromatase activity by 31–34%.

In all the experiments, Sant 7 induced a dramatic reduction in aromatase activity in cells stimulated by IL-6 plus Il-6 sR. This marked reduction brought aromatase activity to basal levels or lower. The results presented in FIG. 2 show that pretreatment of the fibroblasts with Sant 7 is not necessary to block aromatase activity. In fact, in the experiment in which the fibroblasts were not pretreated, the results obtained were the same.

The results reported in FIG. 4 show that the inhibitory effect on aromatase activity induced by Sant 7 is dose-dependent. At concentrations as low as 0.1 μg/mL a drastic reduction (approximately 75%) in aromatase activity is observed. Maximum inhibition (90%) is obtained at the 10 μg/mL concentration. From the curve obtained with the various different concentrations it proved possible to obtain the $IC_{50}$ value, that is to say the Sant 7 concentration with which 50% inhibition of aromatase activity is obtained. This value was 0.06 μg/mL.

The invention claimed is:

1. A method of treating a breast tumour or other fibroblast-implicated tumour mediated by an increase in aromatase activity, said method comprising administration of a compound comprising an amino acid sequence selected from the group consisting of SEQ ID NO:4, SEQ ID NO:5, SEQ ID NO:6, and SEQ ID NO:7 (Sant 7) for treatment of said tumour.

2. The method according to claim 1, wherein said compound inhibits at least one enzyme catalyzing oestrogen synthesis selected from the group consisting of aromatase, oestrone sulphatase, and oestradiol dehydrogenase.

3. The method according to claim 1, wherein said compound is Sant 7.

4. A method of inhibiting oestrogen synthesis, said method comprising reducing activity of one or more enzymes catalyzing oestrogen synthesis selected from the group consisting of aromatase, oestrone sulphatase, and oestradiol dehydrogenase with a compound which comprises an amino acid sequence selected from the group consisting of SEQ ID NO:4, SEQ ID NO:5, SEQ ID NO:6, and SEQ ID NO:7 (Sant 7) such that said oestrogen synthesis is inhibited.

5. The method according to claim 4, wherein said compound consists essentially of an amino acid sequence selected from the group consisting of SEQ ID NO:4, SEQ ID NO:5, SEQ ID NO:6, and SEQ ID NO:7 (Sant 7).

6. The method according to claim 4, wherein oestrogen synthesis is inhibited in an oestrogen-dependent tumour.

7. The method according to claim 4, wherein oestrogen synthesis is inhibited in a breast tumour.

8. The method according to claim 4, wherein said compound is Sant 7.

* * * * *